United States Patent [19]

Ulrich et al.

[11] Patent Number: 5,356,895
[45] Date of Patent: Oct. 18, 1994

[54] 1,4 PIPERIZINO INHIBITORS OF NON-ENZYMATIC CROSS-LINKING OF PROTEINS

[75] Inventors: Peter C. Ulrich, Tenafly, N.J.; Anthony Cerami, Shelter Island, N.Y.

[73] Assignee: The Rockefeller University, New York, N.Y.

[21] Appl. No.: 889,141

[22] Filed: May 27, 1992

Related U.S. Application Data

[60] Division of Ser. No. 605,654, Oct. 30, 1990, Pat. No. 5,140,048, which is a continuation-in-part of Ser. No. 264,930, Nov. 2, 1988, Pat. No. 4,983,604, which is a continuation-in-part of Ser. No. 119,958, Nov. 13, 1987, Pat. No. 4,908,446, which is a continuation-in-part of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.$^5$ ................. C07D 241/04; A61K 31/495
[52] U.S. Cl. .................................... 514/255; 544/402
[58] Field of Search ................ 544/370, 402; 514/255

[56] References Cited

U.S. PATENT DOCUMENTS

| | | | |
|---|---|---|---|
| 4,665,192 | 5/1987 | Cerami | 548/336 |
| 4,758,583 | 7/1988 | Cerami et al. | 514/399 |
| 4,908,446 | 3/1990 | Ulrich et al. | 540/533 |
| 5,140,048 | 8/1992 | Ulrich et al. | 514/601 |

*Primary Examiner*—David B. Springer
*Attorney, Agent, or Firm*—Klauber & Jackson

[57] ABSTRACT

The present invention relates to compositions and methods for inhibiting nonenzymatic cross-linking (protein aging). Accordingly, a composition is disclosed which comprises; an agent capable of inhibiting the formation of advanced glycosylation endproducts of target proteins by reacting with the carbonyl moiety of the early glycosylation product of such target proteins formed by their initial glycosylation. Suitable agents contain an active nitrogen-containing group, such as a hydrazine group. Particular agents comprise aminoguanidine derivatives. the method comprises contacting the target protein with the composition. Both industrial and therapeutic applications for the invention are envisioned, as food spoilage and animal protein aging can be treated.

3 Claims, No Drawings

1,4 PIPERIZINO INHIBITORS OF NON-ENZYMATIC CROSS-LINKING OF PROTEINS

This invention was made in part with government support under Grant Number PH S AM 19655 awarded by the National Institutes of Health. The Government has certain rights in the invention.

CROSS REFERENCE TO RELATED APPLICATIONS

This is a division of application Ser. No. 07/605,654, filed Oct. 30, 1990, now U.S. Pat. No. 5,140,048 which is a continuation-in-part of U.S. application Ser. No. 07/264,930, filed Nov. 2, 1988, now U.S. Pat. No. 4,983,604, which is a continuation-in-part of copending application Ser. No. 119,958, filed Nov. 13, 1987, now U.S. Pat. No. 4,908,446, which is a Continuation-In-Part of copending application Ser. No. 798,032, filed Nov. 14, 1985, now U.S. Pat. No. 4,758,583, which is a continuation-in-part of application Ser. No. 590,820, filed Mar. 19, 1984 and now U.S. Pat. No. 4,665,192, issued May 12, 1987, by Anthony Cerami.

RELATED PUBLICATIONS

The Applicants are co-authors of the following articles directed to the subject matter of the present invention: "COVALENT ATTACHMENT OF SOLUBLE PROTEINS BY NONENZYMATICALLY-GLYCOSYLATED COLLAGEN: ROLE IN THE IN SITU FORMATION OF IMMUNE COMPLEXES", Brownlee M., Pongor S., Cerami A., (1983), *J. Exp. Med.*, 158, pp. 1730-1744; and "AGING OF PROTEINS: ISOLATION AND IDENTIFICATION OF FLUORESCENT CHROMOPHORE FROM THE REACTION OF POLYPEPTIDES WITH GLUCOSE", Pongor, et al, *Proc. Natl. Acad. Sci. USA*, 81, pp. 2684-2688, (May, 1984), both of which are incorporated herein by reference.

BACKGROUND OF THE INVENTION

The present invention relates generally to the reaction that occurs between glucose and proteins, and more particularly to the inhibition by various aminoguanidine derivatives of the reaction of nonenzymatically glycosylated proteins leading to advanced glycosylation end products.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Maillard, *C. R. Acad. Sci.*, 154, pp. 66-68, (1912).

In the years that followed the initial discovery by Maillard, food chemists studied the hypothesized reaction in detail and determined that stored and heat treated foods undergo nonenzymatic browning as a result of the reaction between glucose and the polypeptide chain, and that the proteins are resultingly cross-linked and correspondingly exhibit decreased bioavailability. Finot, P. A. (1982) in *Modification of Proteins*, eds, Feehey, R. E. and Whitaker, J. R., *American Chemical Society*, 198, pp. 91-124, Washington, D.C. At this point, it was determined that the pigments responsible for the development of the brown color that develops as a result of protein glycosylation possessed characteristic spectra and fluorescent properties. However, the chemical structure of the pigments had not been specifically elucidated.

The reaction between reducing sugars and food proteins discussed above was found in recent years to have its parallel in vivo. Thus, the nonenzymatic reaction between glucose and the free amino groups on proteins to yield the Amadori product, has been shown to occur with hemoglobin, wherein a rearrangement of the amino terminal of the beta-chain of hemoglobin by reaction with glucose, forms the adduct known as hemoglobin $A_{1c}$. The reaction has also been found to occur with a variety of other body proteins, such as lens crystallins, collagen and nerve proteins. See, Bunn et al, *Biochem. Biophys. Res. Comm.*, 67, pp. 103-109 (1975); Koenig et al, *J. Biol. Chem.*, 252, pp. 2992-2997 (1977); Monnier, and Cerami, A., in *Maillard Reaction in Food add Nutrition*, ed. Waller, G. A., *American Chemical Society*, 215, pp.431-448 (1983); and Monnier and Cerami, *Clinics in Endocrinology and Metabolism*, 11, pp. 431-452 (1982). Moreover, brown pigments with spectral and fluorescent properties similar to those of late-stage Maillard products have also been observed in vivo in association with several long-lived proteins, such as lens proteins and collagen from aged individuals. An age related linear increase in pigment was observed in human dura collagen between the ages of 20 to 90 years. See, Monnier, and Cerami, *Science*, 211, pp. 491-493 (1981); Monnier, and Cerami, *Biochem. Biophys. Acta*, 760, pp. 97-103 (1983); and, Monnier et al., "Accelerated Age-Related Browning of Human Collagen in Diabetes Mellitus", *Proc. Nat. Acad. Sci.*, 81, pp. 583-587 (1984). Interestingly, the aging of collagen can be mimicked in vitro by the cross-linking induced by glucose; and the capture of other proteins and the formation of adducts by collagen, also noted, is theorized to occur by a cross-linking reaction, and is believed to account for the observed accumulation of albumin and antibodies in kidney basement membrane. See, Brownlee et al, *J. Exp. Med.*, 158, pp. 1739-1744 (1983); and Kohn et al, *Diabetes*, 33, No. 1, pp. 57-59 (1984).

2-Furoyl-4(5)-2(furanyl)-1H-imidazole has been isolated from the acid hydrolysates of browned proteins and is believed to be a cross-linker from the nonenzymatic browning of proteins, Pongor et al., *Proc. Natl. Acad. Sci.* USA, 81, 2684 (1984), and U.S. Pat. No. 4,665,192, issued May 12, 1987, and entitled "Methods and Agents for Measuring Protein Aging".

Methods of inhibiting the Maillard reaction in vivo using aminoguanidine are known, Brownlee et al., *Science*, 232, 1629 (1986), and U.S. Pat. No. 4,758,583, issued Jul. 19, 1988, and entitled "Method and Agents for Inhibiting Protein Aging". In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned. The mechanism for the allergic reaction is not known. A need thus exists for a suitable agent for the inhibition of nonenzymatic browning for use in processed and stored foods, as well as in various other pharmaceutical and diagnostic products.

Additionally, the discovery of a suitable agent for the inhibition of nonenzymatic cross-linking would provide a means of reducing or obviating the effects of protein aging, especially in such disease states as diabetes mellitus, etc.

SUMMARY OF THE INVENTION

In accordance with the present invention, a method and associated agents are disclosed for the inhibition of nonenzymatic cross-linking (protein aging). In particular, agents for inhibiting nonenzymatic cross-linking (protein aging) due to the formation of advanced glycosylation end products may be selected from those materials capable of reacting with the early glycosylation product from the reaction of glucose with proteins and preventing further reactions.

The compounds have the following-structural formula:

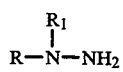
(I)

wherein R is a group of the formula

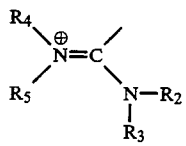

and $R_1$ is hydrogen or a lower alkyl group of 1–6 carbon atoms, a hydroxyethyl group, or together with $R_2$ may be a lower alkylene bridge of 2–4 carbon atoms;

$R_2$ is hydrogen or a lower alkyl group of 1–6 carbon atoms or together with $R_1$ or $R_3$ is a lower alkylene bridge of 2–4 carbon atoms, amino, hydroxy, or an aminoalkylene group of the formula

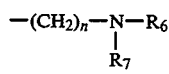

wherein n is an integer of 2–7 and $R_6$ and $R_7$ are independently a lower alkyl group of 1–6 carbon atoms or together form a part of a heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring, it may be optionally substituted by a substituent that is identical to the portion of the compound on the first nitrogen of the piperazine ring.

$R_3$ is hydrogen, a lower alkyl group of 1–6 carbon atoms, or together with $R_2$ or $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms; with the proviso that at least one of $R_1$, $R_2$, $R_3$, $R_4$ or $R_5$ is other than hydrogen;

or R is an acyl or a lower alkylsulfonyl group of up to ten carbon atoms and $R_1$ is hydrogen;

and their pharmaceutically acceptable acid addition salts.

Certain of the compounds of formula I are represented by the formula II

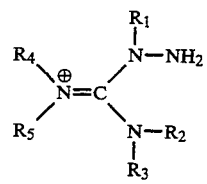
(II)

wherein $R_1$ is hydrogen or a lower alkyl group of 1–6 carbon atoms, a hydroxyethyl group, or together with $R_2$ may be a lower alkylene bridge of 2–4 carbon atoms;

$R_2$ is hydrogen or a lower alkyl group of 1–6 carbon atoms or together with $R_1$ or $R_3$ is a lower alkylene bridge of 2–4 carbon atoms, amino, hydroxy, or an aminoalkylene group of the formula

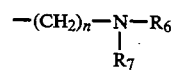

wherein n is an integer of 2–7 and $R_6$ and $R_7$ are independently a lower alkyl group of 1–6 carbon atoms or together form a heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring, it may be optionally substituted by a substituent that is identical to the portion of the compound on the first nitrogen of the piperazine ring.

$R_3$ is hydrogen, a lower alkyl group of 1–6 carbon atoms, or together with $R_2$ or $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms; with the proviso that at least one of $R_1$, $R_2$, $R_3$, $R_4$ or $R_5$ is other than hydrogen;

and their pharmaceutically acceptable acid addition salts.

Thus, certain of the compounds of this invention are substituted aminoguanidine derivatives.

Certain of the aminoguanidine derivatives useful in the method of the present invention are novel compounds. Correspondingly, the present invention relates to these novel compounds, as well as to their methods. Certain of these novel compounds are represented by the formula III

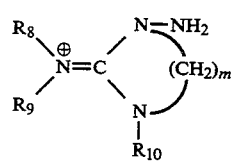
(III)

wherein $R_8$ is amino, hydrogen, 2-hydroxyethyl or lower alkyl, $R_9$ and $R_{10}$ are hydrogen, 2-hydroxyethyl, or a lower alkyl group with the proviso that at least one of $R_8$, $R_9$, and $R_{10}$ is other than hydrogen or lower alkyl, and m is an integer of 2–4. Certain compounds of this group are also represented by the formula

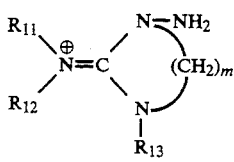 (IV)

wherein $R_{11}$, $R_{12}$ and $R_{13}$ are hydrogen or a lower alkyl group and m is an integer of 2–4.

Specifically preferred compounds are those wherein $R_8$, $R_9$ and $R_{10}$ are all hydrogen and those wherein m=2.

Other novel compounds of this invention are those compounds of formula II wherein $R_6$ and $R_7$ together with the nitrogen atom are a morpholino group. These are thus represented by the formula

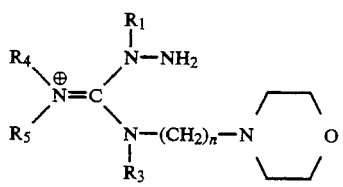

wherein $R_1$ is hydrogen or a lower alkyl group of 1–6 carbon atoms; a hydroxyethyl group, n is an integer of 2–7;

$R_3$ is hydrogen, a lower alkyl group of 1–6 carbon atoms, or together with $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms; with the proviso that at least one of $R_1$, $R_3$, $R_4$ or $R_5$ is other than hydrogen; and their pharmaceutically acceptable acid addition salts.

Also novel are the group of compounds of formula II where $R_1$ is a hydroxyethyl group. These are thus represented by the formula

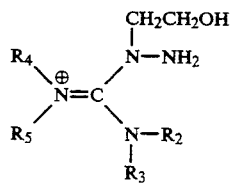

wherein $R_2$ is hydrogen or a lower alkyl group of 1–6 carbon atoms or together with $R_3$ is a lower alkylene bridge of 2–4 carbon atoms, amino, hydroxy or an aminoalkylene group of the formula

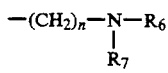

wherein n is an integer of 2–7 and $R_6$ and $R_7$ are independently a lower alkyl group of 1–6 carbon atoms or together with the nitrogen atom are a morpholino or piperidino group;

$R_3$ is hydrogen, a lower alkyl group of 1–6 carbon atoms, or together with $R_2$ or $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms; and their pharmaceutically acceptable acid addition salts.

The compounds of this invention appear to react with the glycosylation product thereby preventing the same from later forming the advanced glycosylation end products which lead to protein crosslinks, and thereby, to protein aging.

The present invention also relates to a method for inhibiting protein aging by contacting the initially glycosylated protein at the stage of the early glycosylation product with a quantity of one or more of the agents of the present invention. In the instance where the present method has industrial application, one or more of the agents may be applied to the proteins in question, either by introduction into a mixture of the same in the instance of a protein extract, or by application or introduction into foodstuffs containing the protein or proteins, all to prevent premature aging and spoilage of the particular foodstuffs.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 25 mg/kg.

The ability to inhibit the formation of advanced glycosylation end products carries with it significant implications in all applications where protein aging is a serious detriment. Thus, in the area of food technology, economic and social benefit by making certain foods of marginal stability less perishable and therefore more available for consumers. Spoilage would be reduced as would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, might be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as one of the sequelae of diabetes. Consequently, the ability to either retard or substantially inhibit the formation of advanced glycosylation end products carries the promise of treatment for diabetes and of course, improving the quality and, perhaps, duration of animal life.

Accordingly, it is a principal object of the present invention to provide a method for inhibiting the extensive cross-linking of proteins that occurs as an ultimate consequence of the reaction of the proteins with glucose, by correspondingly inhibiting the formation of advanced glycosylation end products.

It is a further object of the present invention to provide a method as aforesaid which is characterized by a reaction with an initially glycosylated protein identified as early glycosylation products.

It is a further object of the present invention to provide a method as aforesaid which prevents the rearrangement and cross-linking of the said early glycosylation products to form the said advanced glycosylation end products.

It is a yet further object of the present invention to provide agents capable of participating in the reaction with the said early glycosylation products in the method as aforesaid.

It is a still further object of the present invention to provide therapeutic methods of treating the adverse consequences of protein aging, manifest in the embrittlement of animal protein and the browning and spoilage of foodstuffs.

It is a still further object of this invention to provide therapeutic methods which only minimally affect the mammalian enzyme diamine oxidase.

Other objects and advantages will become apparent to those skilled in the art from a consideration of the ensuing description.

DETAILED DESCRIPTION

In accordance with the present invention, compositions and associated methods have been developed which are believed to inhibit the formation of advanced glycosylation end products in a number of target proteins existing in both animals and plant material. In particular, the invention relates to a composition which may contain one or more aminoguanidine derivatives of the formula $$R-\underset{\underset{\text{\Large }}{|}}{\overset{R_1}{N}}-NH_2 \qquad (I)$$

wherein R is a group of the formula

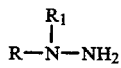

and $R_1$ is hydrogen or a lower alkyl group of 1–6 carbon atoms, a hydroxyethyl group, or together with $R_2$ may be a lower alkylene bridge of 2–4 carbon atoms;

$R_2$ is hydrogen or a lower alkyl group of 1–6 carbon atoms or together with $R_1$ or $R_3$ is a lower alkylene bridge of 2–4 carbon atoms, amino, hydroxy, or an aminoalkylene group of the formula

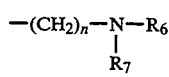

wherein n is an integer of 2–7 and $R_6$ and $R_7$ are independently a lower alkyl group of 1–6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring, it may be optionally substituted by a substituent that is identical to the portion of the compound on the first nitrogen of the piperazine ring.

$R_3$ is hydrogen, a lower alkyl group of 1–6 carbon atoms, or together with $R_2$ or $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms; with the proviso that at least one of $R_1$, $R_2$, $R_3$, $R_4$ or $R_5$ is other than hydrogen; or R is an acyl or a lower alkylsulfonyl group of up to ten carbon atoms and $R_1$ is hydrogen;

and their pharmaceutically acceptable acid addition salts.

Certain of these compositions contain compounds of the formula

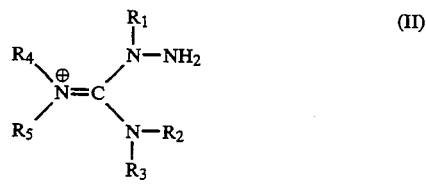

wherein $R_1$ is hydrogen or a lower alkyl group of 1–6 carbon atoms, a hydroxyethyl group, or together with $R_2$ may be a lower alkylene bridge of 2–4 carbon atoms;

$R_2$ is hydrogen or a lower alkyl group of 1–6 carbon atoms or together with $R_1$ or $R_3$ is a lower alkylene bridge of 2–4 carbon atoms, amino, hydroxy, or an aminoalkylene group of the formula

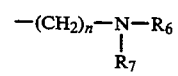

wherein n is an integer of 2–7 and $R_6$ and $R_7$ are independently a lower alkyl group of 1–6 carbon atoms or together with the nitrogen atom are a morpholino or piperidino group;

$R_3$ is hydrogen, a lower alkyl group of 1–6 carbon atoms, or together with $R_2$ or $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms;

with the proviso that at least one of $R_1$, $R_2$, $R_3$, $R_4$ or $R_5$ is other than hydrogen;

and their pharmaceutically acceptable acid addition salts.

The lower alkyl and lower alkoxy groups referred to herein contain 1–6 carbon atoms and include methyl, methoxy, ethyl, ethoxy, propyl, propoxy, butyl, butoxy,

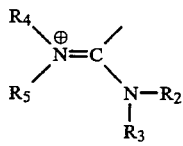

pentyl, pentyloxy, hexyl, hexyloxy and the corresponding branched chain isomers thereof.

The acyl radicals referred to herein are residues of lower alkyl, aryl and heteroaryl carboxylic acids containing 2–10 carbon atoms. They are typified by acetyl, propionyl, butanoyl, valeryl, hexanoyl and the corresponding higher chain and branched chain analogs thereof. The acyl radicals may also contain one or more double bonds and/or an additional acid functional group, e.g., glutaryl or succinyl. The heteroaryl groups referred to above encompass aromatic heterocyclic groups containing 3–6 carbon atoms and one or more heteroatoms such as oxygen, nitrogen or sulfur.

The lower alkyl sulfonyl groups of the compounds of this invention are those containing from 1 to 7 carbon atoms and are typified by methylsulfonyl, ethylsulfonyl, n-propylsulfonyl, t-butylsulfonyl and the like.

The term "aryl" as used herein refers to phenyl and lower alkyl substituted phenyl groups containing 6–10 carbon atoms and substituted by one or more substituent groups selected from among chloro, bromo, fluoro, carboxy, lower alkyl, hydroxy, or lower monoalkylamino, lower dialkylamino, lower alkoxy.

The compounds are capable of inhibiting the formation of advanced glycosylation end products on such target proteins, by reacting with the carbonyl moiety of the early glycosylation product that is formed by the initial glycosylation of the protein.

It is the carbonyl group located near the junction between sugar and protein segments of the early glycosylation product that is theorized to comprise an active site that causes the further cross-linking of the protein to form the advanced glycosylation end product, and likewise contributes to the entrapment of other proteins that is evident in the development in vivo of conditions such as skin wrinkling, certain kidney diseases, atherosclerosis, osteoarthritis and the like. Similarly, plant material that undergoes nonenzymatic browning deteriorates and, in the case of foodstuffs, become spoiled and inedible. Thus, the reaction of the compounds of this invention with this carbonyl moiety is believed to inhibit the late stage Maillard effect.

The rationale of the invention is to use agents which block the post-glycosylation step, i.e., the formation of fluorescent chromophores such as that identified in Pongor, et al., supra. whose presence is associated with, and leads to, the adverse sequelae of diabetes and aging. An ideal agent would prevent the formation of the chromophore and its associate cross-links of proteins to proteins and trapping of proteins on the other proteins, such as occurs in arteries and in the kidney.

Accordingly, the compositions useful in the present invention comprise or contain agents capable of reacting with the active carbonyl intermediate of the early glycosylation product. Suitable agents are the hydrazine derivatives which bear an electron-withdrawing group of the present invention. These agents possess an active nitrogen-containing substituent that is believed to react with the carbonyl of the early glycosylation product. Consequently, reaction of the agents with the glycosyllysine moiety of a protein would prevent this moiety from forming crosslinks with other groups.

Hollis and Strickberger (*Diabetologia* 28:282-5 [1985]) found that in vivo administration of the compound alpha-hydrazinohistidine, a known inhibitor of the enzyme histidine decarboxylase, reduces the accumulation of albumin in the aortas of rats. The authors proposed that the drug acted to reduce production of histamine in this tissue, and that histamine is therefore the mediator of low density lipoprotein accumulation which is implicated in atherosclerotic disease. The findings of Hollis and Strickberger are distinguishable from the concept and application of the present invention on several grounds. The mechanism of histamine synthesis suppression by alpha-hydrazinohistidine suggested by the authors, is functionally distinct from the underlying concept of the present invention, and it is believed, may even be placed in question by the latter. Additionally, one should note that alpha-hydrazinohistidine has no electron-withdrawing group attached to the hydrazine moiety and would not be expected to react efficiently and irreversibly with a glycosylation product.

Thus, the agents of the present invention have been identified and tested on the basis of their ability to react with the carbonyl moiety of the early glycosylation product to form a highly stable adduct, and would not have been suggested from the work of Hollis and Strickberger. In particular, aminoguanidine is known to increase levels of histamine (See Lindberg and Tornqvist, "The Inhibitory Effect of Aminoguanidine on Histamine Catabolism in Human Pregnancy", *Acta Obstet. Gynecol. Scand.*, 45: 131–139, (1966) and alpha-hydrazinohistidine and aminoguanidine therefore have opposing effects on histamine levels. It can therefore by seen that the present findings that both alpha-hydrazinohistidine and aminoguanidine have efficacy in vivo and in vitro to reduce protein cross-linking rules out from consideration and consequently distinguishes the mechanism proposed by Hollis and Strickberger as the explanation of the manner in which the compounds of the present invention might work to reduce advanced glycosylation end product formation.

In the instance where the composition of the present invention is utilized for in vivo or therapeutic purposes, it may be noted that the compounds or agents used therein are biocompatible. Pharmaceutical compositions may be prepared with a pharmaceutically effective quantity of the agents or compounds of the present invention and may include a pharmaceutically acceptable carrier, selected from known materials utilized for this purpose. Such compositions may be prepared in a variety of forms, depending on the method of administration. For example, a compound may be converted to the hydrochloride salt from the commercially available bicarbonate salt to improve its solubility and to make it less irritating for intraperitoneal injection. Various other pharmaceutically acceptable acid addition salts of the compounds of formulae I, II and III may likewise be utilized. Such acid addition salts may be derived from a variety of organic and inorganic acids such as sulfuric, phosphoric, p-toluenesulfonic, hydrochloric, hydrobromic, hydroiodic, sulfamic, citric, lactic, maleic, succinic, tartaric, cinnamic, acetic, benzoic, gluconic, ascorbic and related acids. Also, a liquid form would be utilized in the instance where administration is by intravenous or intraperitoneal injection, while if appropriate, tablets, capsules, etc., may be prepared for oral administration. For topical or dermal application to the skin or eye, a solution, lotion or ointment may be formulated with the agent in a suitable vehicle such as water, ethanol, propylene glycol, perhaps including a carrier to aid in penetration into the skin or eye. Other suitable forms for administration to other body tissues are also contemplated.

The present invention likewise relates to methods for inhibiting the formation of advanced glycosylation end products, which comprise contacting the target proteins with the composition of the present invention. In the instance where the target proteins are contained in foodstuffs, whether plant of animal origin, these foodstuffs could have applied to them by various conventional means a composition containing the present agents. Likewise, in the instance where therapeutic applications are intended, the animals to be treated would have administered to them a regular quantity of the pharmaceutical composition of the present invention. Administration could take place for example daily, and an effective quantity of the agent or compound of the present invention could range up to 25 mg/kg of body weight of the animal. A topical preparation may, for example, include up to 10% of the agent or composition in an ointment or lotion for application to the skin.

Naturally, some variation in these amounts is possible, and the suggested amounts are provided in fulfillment of applicants' duty to disclose the best mode for the practice of the present invention.

As is apparent from a discussion of the environment of the present invention, the present methods and compositions hold the promise for arresting the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with non-toxic, biocompatible compounds is a further advantage of the present invention.

The therapeutic implications of the present invention relate to the arrest of the aging process which has as indicated earlier, been identified in the aging of key proteins by advanced glycosylation and cross-linking. Thus, body proteins such as collagen, elastin, lens proteins, nerve proteins and kidney glomerular basement membranes would all benefit in their longevity and operation from the practice of the present invention. It is further theorized that the present invention would reduce the incidence of pathologies involving the entrapment of proteins by cross-linked target proteins, such as atherosclerosis, osteoarthritis, periarticular rigidity, loss of elasticity and wrinkling of skin, stiffening of joints, glomerulonephritis, diabetic kidney disease, glomerulosclerosis, peripheral vascular disease, atherosclerosis, arteriosclerosis obliterans, peripheral neuropathy, retinopathy, cataract, stroke, hypertension, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies.

The aminoguanidine derivatives encompassed by formula I are conveniently prepared by chemical syntheses well known in the art. Certain of the compounds encompassed by formula I are known compounds readily available from chemical supply houses and/or preparable by synthetic methods specifically published therefor. The novel compounds of formulae III and IV are prepared by analogous routes. For instance, 1,3-diaminoguanidine monohydrochloride and 2-hyrazino-2-imidazoline hydrobromide are available from Aldrich Chemical Company. Acetic acid hydrazide and L-glutamic acid-gamma-hydrazine hydrate can be obtained from Sigma Chemical Company. Methanesulfonyl hydrazide is obtainable from Lancaster Chemical Co. N-hydroxyhydrazinecarboximidamide tosylate can be synthesized according to the procedure of J. Med. Chem., 27, 236–238 (1984). Likewise, the procedure describing 1-methylhydrazinecarboximidamide tosylate is published in J. Med. Chem., 25, 505–518 (1982). N-(3-dimethylaminopropyl) hydrazinecarboximidamide dihydrobromide hydrate is mentioned in U.S. Pat. No. 4,544,759 (1985).

Other compounds described in the chemical and patent literature and encompassed by formula I are:

N-methylhydrazinecarboximidamide;
N-ethylhydrazinecarboximidamide;
N-propylhydrazinecarboximidamide;
N-butylhydrazinecarboximidamide;
N-hexylhydrazinecarboximidamide;
N,N'-dimethylhydrazinecarboximidamide;
N,N'-diethylhydrazinecarboximidamide;
N,N'-diisopropylhydrazinecarboximidamide;
N-(3-diethylaminopropyl)hydrazinecarboximidamide;
N-(2-diethylaminoethyl)hydrazinecarboximidamide;
N-(2-dimethylaminoethyl)hydrazinecarboximidamide;
N-[2-(4-methylpiperazinyl)ethyl]hydrazine-carboximidamide;
N-[2-(1-pyrrolidinyl)ethyl]hydrazinecarboximidamide;
N-[2-(1-piperidinyl)ethyl]hydrazinecarboximidamide;
N-[2-(1-hexahydroazepinyl)ethyl]hydrazinecarboximidamide;
N-[2-(4-methyl-1-hexahydro-1,4-diazepinyl)propyl]-hydrazinecarboximidamide;
N-[2-(1-hexahydroazocinyl)ethyl]hydrazine-carboximidamide;
N-[2-(1-octahydroazoninyl)ethyl]hydrazine-carboximidamide;
N-[2-(2,4-dimethyl-1-pyrrolidinyl)ethyl]-hydrazinecarboximidamide;
acetic acid hydrazide;
aspartic acid $\beta$-hydrazide;
glutamic acid $\tau$-hydrazide; and
methanesulfonic acid hydrazide.

EXAMPLE I

The following methods were used to evaluate the compounds of the present invention for their ability to prevent the glucose-mediated cross-linking of protein in vitro. The test protein utilized is bovine serum albumin (BSA) at a concentration of 100 milligrams per milliliter in a 0.5M sodium phosphate buffer at pH 7.4. Glucose is included in the reaction mixture at a concentration of 200 mM. Sodium azide, 3 mM, is included in all solutions to prevent the growth of microorganisms.

To evaluate compounds, they are included in the above reaction mixture at either 1 mM, 10 mM, or 100 mM. An additional set of incubation mixtures also is prepared in the absence of glucose to serve as baseline controls for each inhibitor. A BSA plus glucose mixture in the absence of any inhibitor serves as an indication of the maximum amount of cross-linking that can occur in each mixture.

After incubation of the mixtures for three weeks at 37° C., the BSA in each mixture must be isolated from the other components of the mixture before the degree of browning is determined. This is necessary because many of the inhibitors are either fluorescent themselves or quench the fluorescence of the browned BSA. To effect the separation, the BSA is precipitated by the addition of 1.0 milliliters of saturated ammonium sulfate to each 100 microliters of incubation mixture. The resulting precipitate is centrifuged and the supernatant solutions are discarded. The precipitate is washed once with saturated ammonium sulfate, then the BSA pellet is redissolved in 1 milliliter of phosphate-buffered saline (PBS) to give a final protein concentration of about 10 milligrams per milliliter.

The actual protein concentration of the BSA solution is determined by a standard dye-binding protein assay. The fluorescence of the BSA is measured in a spectrofluorimeter at an excitation wavelength of 370 nanometers and an emission wavelength of 440 nanometers. This corresponds to the detection of chromophores including FFI which have formed in the BSA as a formation of advanced glycosylation endproducts through the reaction of glycosylated amino groups.

The specific fluorescence of the BSA is measured as fluorescence (in arbitrary units) per milligram of BSA. It is expressed as the increase in fluorescence during the incubation period of the sample incubated with glucose minus the corresponding value in the absence of glucose. The degree of inhibition of each compound is expressed in a percentage scale, where 0% represents no inhibition of browning, i.e., the fluorescence developed in an incubation mixture containing only glucose and BSA, in the absence of any inhibitors. One hundred percent inhibition corresponds to the degree of fluorescence developed in the absence of glucose.

Following the above procedure, the following results were obtained using the test compounds at a concentration of 10 mM.

Percent inhibition of browning by various compounds at 10 mM:

| | |
|---|---|
| 85% | 1,2,3-triaminoguanidine hydrochloride |
| 84% | 1,3-diaminoguanidine monohydrochloride |
| 81% | N-hydroxyhydrazinecarboximidamide tosylate |
| 76% | 2-hydrazino-2-imidazoline hydrobromide |
| 65% | L-glutamic acid-gamma-hydrazide dihydrate |
| 63% | N,N''-3,3'-[1,4-piperazinediylbis(3,1-propanediyl)]bishydrazinecarboximidamide tetrahydrobromide |
| 59% | N-(3-dimethylaminopropyl)hydrazinecarboximidamide dihydrobromide monohydrate |
| 59% | N-(3-(4-methylpiperazin-1-yl)propyl)-hydrazinecarboximidamide trihydrobromide |
| 53% | 1-methylhydrazinecarboximidamide tosylate |
| 49% | methanesulfonic acid hydrazide |
| 48% | acetic acid hydrazide |
| 45% | 1-(2-hydroxyethyl)hydrazinecarboximidamide sulfate 2:1 |
| 44% | aminoguanidine hemisulfate |
| 43% | 1-amino-2-hydrazino-2-imidazoline tosylate |
| 42% | N-(2,2-dimethyl-3-dimethylaminopropyl)hydrazine-carboximidamide dihydrobromide |
| 41% | N-(3-(4-morpholino)propyl)hydrazinecarboximidamide dihydrobromide monohydrate |
| 40% | aminoguanidine hydrochloride |
| 33% | 2-(1-(2-hydroxyethyl)hydrazino)-2-imidazoline sulfate 2:1 |
| 32% | N-(2-(4-morpholino)ethyl)hydrazinecarboximidamide dihydrobromide |
| 0% | no inhibitor |

EXAMPLE 2

Evaluation of test compounds at 1 mM was performed the same way as in Example 1. The results are as follows:

| | |
|---|---|
| 70% | N-ethylhydrazinecarboximidamide 4-methylbenzenesulfonate |
| 67% | 1-amino-2-hydrazino-2-imidazoline tosylate |
| 65% | N-methylhydrazinecarboximidamide 4-methylbenzenesulfonate |
| 46% | 2-(1-(2-hydroxyethyl)hydrazino)-2-imidazoline sulfate 2:1 |
| 42% | 2-hydrazino-2-imidazoline hydrobromide |
| 39% | aminoguanidine acetate |
| 37% | N-hydroxyhydrazinecarboximidamide tosylate |
| 37% | 1,2,3-triaminoguanidine hydrochloride |
| 37% | N,N''-3,3'-[1,4-piperazinediylbis(3,1-propanediyl)]bishydrazinecarboximidamide tetrahydrobromide |
| 33% | 1,2-diamino-2(1H)-imidazoline tosylate |
| 31% | 1,3-diaminoguanidine monohydrochloride |
| 26% | acetic acid hydrazide |
| 24% | L-glutamic acid-gamma-hydrazide dihydrate |
| 23% | N-(3-dimethylaminopropyl)hydrazinecarboximidamide dihydrobromide monohydrate |
| 23% | N-(3-(4-methylpiperazin-1-yl)propyl)-hydrazinecarboximidamide trihydrobromide |
| 22% | beta-aspartic hydrazide |
| 21% | 1-(2-hydroxyethyl)hydrazinecarboximidamide sulfate 2:1 |
| 21% | methanesulfonic acid hydrazide |
| 19% | aminoguanidine hydrochloride |
| 0% | no inhibitor |

EXAMPLE 3

Evaluation of test compounds at 100 mM was performed the same way as in Example 1. The results are as follows:

Percent inhibition of browning by various compounds at 100 mM.

| | |
|---|---|
| 100 % | N,N''-3,3'-[1,4-piperazinediylbis(3,1-propanediyl)]bishydrazinecarboximidamide tetrahydrobromide |
| 98% | L-glutamic acid-gamma-hydrazide dihydrate |
| 98% | 1,3-diaminoguanidine monohydrochloride |
| 97% | N-(2,2-dimethyl-3-dimethylaminopropyl)hydrazine-carboximidamide dihydrobromide |
| 96% | N-hydroxyhydrazinecarboximidamide tosylate |
| 96% | N-3(4-methylpiperazin-1-yl)propyl)-hydrazinecarboximidamide trihydrobromide |
| 95% | 2-hydrazino-2-imidazoline hydrobromide |
| 94% | aminoguanidine hemisulfate |
| 93% | methanesulfonic acid hydrazied |
| 93% | N-(3-(4-morpholino)propyl)hydrazinecarboximidamide dihydrobromide monohydrate |
| 92% | N-(3-dimethylaminopropyl)hydrazinecarboximidamide dihydrobromide monohydrate |
| 91% | aminoguanidine methanesulfonate |
| 90% | N-(2-(4-morpholino)ethylhydrazinecarboximidamide dihydrobromide |
| 90% | 1-amino-2-hydrazino-2-imidazoline tosylate |
| 88% | aminoguanidine hydrochloride |
| 81% | 2-(1-(2-hydroxyethyl)hydrazino)-2-imidazoline sulfate 2:1 |
| 0% | no inhibitor |

The in vitro experiments of Examples 1–3 indicate that this type of drug therapy has benefit in reducing the pathology associated with the advanced glycosylation of proteins and the formation of crosslinks between proteins and other macromolecules. Drug therapy may be used to prevent the increased trapping and cross-linking of proteins that occurs in diabetes and aging which leads to sequelae such as retinal damage, and extra-vascularly, damage to tendons, ligaments and other joints. This therapy might retard atherosclerosis and connective tissue changes that occur with diabetes and aging. Both topical, oral, and parenteral routes of administration to provide therapy locally and systemically are contemplated.

EXAMPLE 4

Certain of the novel aminoguanidine derivatives are synthesized in the following manner.

N-(3-(4-morpholino)propyl]hydrazinecarboximidamide dihybrobromide

Hydrazinecarboximidothioic acid ethyl ester hydrobromide (10.0 grams) and 3-(4-morpholino)propylamine (7.56 grams) are dissolved in ethanol (20 milliliters) and kept at room temperature for 2 days, then heated at reflux for 30 minutes. Isopropanol (20 milliliters) is added, and the mixture is cooled and treated with 48% hydrobromic acid (6 milliliters). Additional ethanol (50 milliliters) and isopropanol (20 milliliters) are added and the mixture is stored at −20° C. for two days. The crystalline precipitate is triturated, filtered out and washed with ethanol and isopropanol, giving 14.91 grams of crystalline solid. To purifying this material, 11 grams are dissolved in 16.5 milliliters of water, filtered to remove insoluble material, and diluted with 5.5 milliliters of methanol and 100 milliliters of isopropanol. After storage at room temperature and at 4° C., the precipitate is filtered out and washed with isopropanol, giving 9.0 grams of colorless crystals of the title compound, melting point of 129–130° C.

Following analogous procedures, the following aminoalkyl hydrazinecarboximidamide derivatives are prepared (substituting for 3-(4-morpholino)propylamine the following reagents):

From 2-(4-morpholino)ethylamine, the compound N-(2-(4-morpholino)ethyl) hydrazinecarboximidamide dihydrobromide, melting point 169°–171° C.

From 3-(4-methylpiperazin-1-yl)propylamine, the compound N-(3-(4-methylpiperazin-1-yl)propyl)hydrazinecarboximidamide trihydrobromide, melting point 212° C.

From 2,2-dimethyl-3-dimethylaminopropylamine, the compound N-(2,2-dimethyl-3-dimethylaminopropyl)hydrazinecarboximidamide dihydrobromide, melting point 105°–107° C.

From 1,4-piperazinediylbis(3,1-propylamine), the compound N,N″-[1,4-piperazinediylbis(3,1-propanediyl)]bishydrazine-carboximidamide tetrahydrobromide, melting point 241°–244° C.

From 3-dimethylaminopropylamine, the compound N-(3-dimethylaminopropyl)hydrazinecarboximidamide dihydrobromide, melting point 82°–84° C.

EXAMPLE 5

1-(2-hydroxyethyl)hydrazinecarboximidamide sulfate 2:1

Carbimidothioic acid methyl ester sulfate 2:1 (6.955 grams) and 2-hydroxyethylhydrazine (9.13 grams) are stirred and heated at 40° C. for one hour. Methanol (20 milliliters) is added and the mixture is heated at reflux for four hours. On cooling, crystals separate. Filtration gives 5.34 grams of colorless crystals. Three recrystallizations from 88% methanol afford 4.111 grams of the title compound as colorless crystals, melting point 178.5°–180° C.

EXAMPLE 6

2-(1-(2-hydroxyethyl) hydrazino)-2-imidazoline sulfate (2:1)

2-Methylthio-2-imidazoline sulfate (2:1) (1.98 g) and 2-hydroxyethylhydrazine (2.12 g) are heated in ethanol (3 ml) at reflux for 1 hr., then stirred at 25° C. for 3 hr. The solution was diluted with ethanol (20 ml) and kept at 4° C. for 18 hours. The crystals which separated were filtered out and washed with ethanol. Weight 811 mg, mp 190°–4° C.

Similarly, from the corresponding S-methylisothiuronium derivatives are prepared the following compounds or their acid addition salts:

2-(1-(2-hydroxyethyl)hydrazino)-3-methyl-1-imidazoline;

2-(1-(2-hydroxyethyl)hydrazino)-4,4-dimethyl-1-imidazoline;

1,3-dimethyl-2-(1-(2-hydroxyethyl)hydrazino)imidazolium;

2-(1-(2-hydroxyethyl)hydrazino)-3,4,5,6-tetrahydropyrimidine;

2-(1-(2-hydroxyethyl)hydrazino)-5,5-dimethyl-3,4,5,6-tetrahydropyrimidine;

2-(1-(2-hydroxyethyl)hydrazino)-5-hydroxy-3,4,5,6-tetrahydropyrimidine;

2-(1-(2-hydroxyethyl)hydrazino)-5,5-dibutyl-3,4,5,6-tetrahydropyrimidine;

2-(1-(2-hydroxyethyl)hydrazino)-3-methyl-3,4,5,6-tetrahydropyrimidine;

1,3-dimethyl-2-(1-(2-hydroxyethyl)hydrazino)-3,4,5,6-tetrahydropyrimidium;

2-(1-(2-hydroxyethyl)hydrazino)-4,5,6,7-tetrahydro-1,3(1H)-diazepine;

2-(1-(2-hydroxyethyl)hydrazino)-4,4,7,7-tetramethyl-4,5,6,7-tetrahydro-1,3(1H)-diazepine;

N-methyl-1-(2-hydroxyethyl)hydrazinecarboximidamide;

N,N′dimethyl-1-(2-hydroxyethyl)hydrazinecarboximidamide;

1-pyrrolidinecarboximidic acid 1-(2-hydroxyethyl)hydrazide;

N-methyl(1-pyrrolidine)carboximidic acid 1-(2-hydroxyethyl)hydrazide;

1-piperidinecarboximidic acid 1-(2-hydroxyethyl) hydrazide;

1-hexahydroazepinecarboximidic acid 1-(2-hydroxyethyl) hydrazide;

1-(4-methylpiperazine)carboximidic acid 1-(2-hydroxyethyl)hydrazide;

1-(4-methylhexahydro-1,4-diazepine)carboximidic acid 1-(2-hydroxyethyl)hydrazide; and 4-morpholinecarboximidic acid 1-(2-hydroxyethyl) hydrazide.

EXAMPLE 7

1,2-Diamino-2-(1H)imidazoline p-toluenesulfonate

1-Aminoimidazolidine-2-thione (2.34 g) and methyl p-toluenesulfonate (4.1 g) in ethanol (15 ml) are heated to reflux for 10 minutes, then kept at room temperature for 16 hours. The crystalline precipitate is filtered out and washed with isopropanol to give 4.613 g of 1-amino-2-methylthio-2-midazoline p-toluenesulfonate as colorless needles, of which 3.79 g is placed in methanol (15 ml) and treated with concentrated aqueous ammonia. After stirring for 6 hours, the mixture is diluted with 20 ml isopropanol. After another 12 hours, 5 ml of liquid is distilled off at atmospheric pressure, and 10 ml isopropanol is added to the remainder. The crystals which separate on cooling are filtered out and washed with isopropanol to give 2.323 g of 1,2-diamino-2(1H)-imidazoline p-toluenesulfonate, melting point 190°–190.5° C.

EXAMPLE 8

1-amino-2-hydrazino-2-imidazoline p-toluenesulfonate

1-Amino-2-methylthio-2-imidazoline p-toluenesulfonate (2.123 g) in ethanol (4 ml) was treated with hydrazine (0.67 ml) and stirred at 25° C. for 2 hours. Isopropyl alcohol (6 ml) was added and after stirring for 10 min the crystalline precipitate was filtered out and washed with isopropyl alcohol to give 1.55 g of 1-amino-2-hydrazino-2-imidazoline p-toluenesulfonate, melting point 168°–169° C.

EXAMPLE 9

The aminoguanidine derivatives of the present invention are tested according to the method of Stoner, *Agents and Actions,* 17, pp. 5–9 (1985) in order to ascertain their lack of ability to inhibit the enzyme diamine oxidase. This enzyme is responsible for detoxifying histamine and therefore it would be desirable in any therapy to avoid inhibition of this enzyme.

Percent Inhibition at 10 micromolar:

| | |
|---|---|
| 92% | Aminoguandine hydrochloride |
| 0% | 1-(2-hydroxyethyl)hydrazinecarboximidamide sulfate 2:1 |
| 0% | 1-methylhydrazinecarboximidamide tosylate |
| 84% | N-hydroxyhydrazinecarboximidamide tosylate |
| 59% | 2-hydrazino-2-imidazoline hydrobromide |
| 92% | 1,3-diaminoguanidine monohydrochloride |
| 0% | N-(3-dimethylaminopropyl)hydrazinecarboximidamide dihydrobromide monohydrate |
| 0% | N-(3-(4-methylpiperazin-1-yl)propyl)-hydrazinecarboximidamide trihydrobromide |
| 12% | N,N''-3,3'[1,4-piperazinediylbis(3,1-propanediyl)]bishydrazinecarboximidamide tetrahydrobromide |
| 82% | 1,2,3-triaminoguanidine hydrochloride |
| 5% | N-(3-(4-morpholino)propyl)hydrazinecarboximidamide dihydrobromide |
| 0% | N-(2,2-dimethyl-3-dimethylaminopropyl)hydrazine-carboximidamide dihydrobromide |
| 9% | 1,2-diamino-2(1H)-imidazoline tosylate |
| 9% | methanesulfonic acid hydrazide |
| 75% | L-glutamic acid-gamma-hydrazide dihydrate |
| 32% | beta-aspartic hydrazide |
| 0% | acetic acid hydrazide |

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A composition for inhibiting the advanced glycosylation of a target protein comprising a compound of the formula

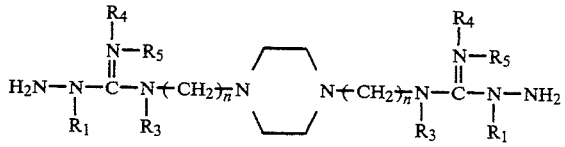

wherein $R_1$ is hydrogen or a lower alkyl group of 1–6 carbon atoms, or a hydroxyethyl group; $R_3$ is hydrogen, or a lower alkyl group of 1–6 carbon atoms; $R_4$ is hydrogen, a lower alkyl group of 1–6 carbon atoms or an amino group; $R_5$ is hydrogen, or a lower alkyl group of 1–6 carbon atoms; and their pharmaceutically acceptable acid addition salts and an acceptable carrier therefor.

2. The compounds of the formula

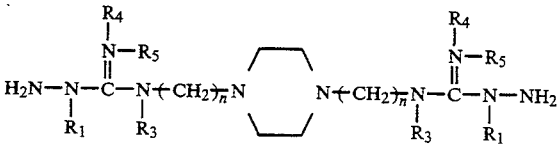

wherein $R_1$ is hydrogen or a lower alkyl group of 1–6 carbon atoms, or a hydroxyethyl group;

$R_3$ is hydrogen, a lower alkyl group of 1–6 carbon atoms;

$R_4$ is hydrogen, a lower alkyl group of 1–6 carbon atoms; or an amino group;

$R_5$ is hydrogen, or a lower alkyl group of 1–6 carbon atoms;

and their pharmaceutically acceptable acid addition salts.

3. The compound according to claim 2 which is N,N''-[1,4-piperazinediylbis(3,1-propanedyl)]-bishydrazinecarboximidamide or a pharmaceutically acceptable acid addition salt thereof.

* * * * *